United States Patent [19]

Chou et al.

[11] Patent Number: 5,189,036
[45] Date of Patent: Feb. 23, 1993

[54] IMIDAZOLYLBENZOYL SUBSTITUTED HETEROCYCLES

[75] Inventors: Yuo-Ling Chou, Piscataway; Paul W. Erhardt, Long Valley; Alfred A. Hagedorn, III, Edison; John W. Lampe, Rockaway, all of N.J.; Lumma, Jr., William C., Pennsburg, Pa.; Thomas K. Morgan, Morris Plains; Jay R. Wiggins, Hamburg, both of N.J.

[73] Assignee: Schering AG, Berlin, Fed. Rep. of Germany

[21] Appl. No.: 540,980

[22] Filed: Jun. 20, 1990

[51] Int. Cl.$^5$ ............... A61K 31/495; A61K 31/445; C07D 401/12; C07D 403/12
[52] U.S. Cl. .................................. 514/252; 514/326; 544/370; 546/210
[58] Field of Search ............ 544/370; 546/210; 514/252, 326

[56] References Cited

U.S. PATENT DOCUMENTS

| 4,804,662 | 2/1989 | Lis et al. | 514/252 |
| 4,851,526 | 7/1989 | Greenberg et al. | 544/370 |
| 4,868,194 | 9/1989 | Can et al. | 514/318 |

FOREIGN PATENT DOCUMENTS 290377 11/1988 European Pat. Off. .

OTHER PUBLICATIONS

Morgan et al. CA 112-158146t (1990).

Primary Examiner—Cecilia Tsang
Attorney, Agent, or Firm—Elizabeth A. Bellamy; John L. White; Anthony J. Zelano

[57] ABSTRACT

Novel imidazolybenzoyl substituted heterocycles and their use as cardiovascular agents most especially as Class III antiarrhythmic agents is described. Pharmaceutical formulations containing such compounds are also discussed.

22 Claims, No Drawings

IMIDAZOLYLBENZOYL SUBSTITUTED HETEROCYCLES

GENERAL DESCRIPTION OF THE INVENTION

Composition-of-Matter Aspect

In its composition-of-matter aspect this invention relates to novel imidazolylbenzoyl substituted heterocycles and their pharmaceutically acceptable salts. Particularly, this invention relates to novel compounds defined by the following Formula I:

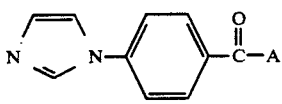

wherein
A is

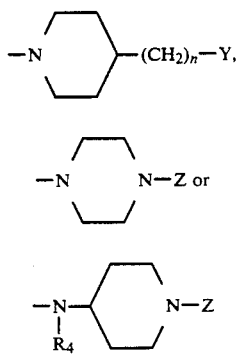

Y is selected from

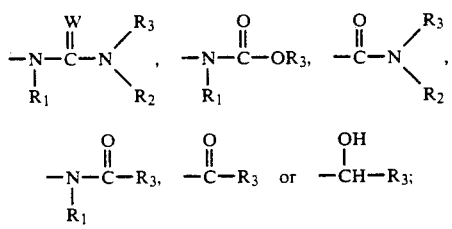

Z is selected from

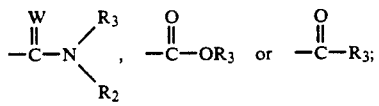

W is selected from O, S, NR, NCN or $CHNO_2$

R is selected from hydrogen, $C_1$-$C_4$ straight or branched chain alkyl, optionally substituted aryl or arylalkyl $R_1$, $R_2$, $R_4$ are independently hydrogen or $C_1$-$C_4$ straight or branched chain alkyl $R_3$ is selected from $C_1$-$C_8$ straight or branched chain alkyl, optionally substituted aryl or arylalkyl, or heteroaryl;

n is selected from the integers 0, 1 or 2, and the pharmaceutically acceptable salts thereof.

Provisos in the foregoing Formula I and definition thereof are that when $R_3$ is a $C_1$-$C_8$ straight or branched chain alkyl this is not inclusive of a tertiary moiety and when $R_3$ is heteroaryl, said heteroaryl cannot be attached to a hetero atom e.g. N or O.

Also contemplated as part of this invention are the pharmaceutically acceptable salts of the compounds of Formula I. Useful acids for this purpose include inorganic acids such as hydrobromic, hydrochloric, sulfuric, phosphoric and organic acids such as acetic, propanoic, benzoic, naphthalenecarboxylic, oxalic, succinic, malic, adipic, lactic, tartaric, citric, salicylic, methanesulfonic and p-toluenesulfonic.

It is to be understood that the definition of the compounds of Formula I encompasses all possible stereoisomers and mixtures thereof, which possess the activity discussed below. In particular, it encompasses racemic modifications and any optical isomers which possess the indicated activity.

It is also to be understood that the definition of the compounds of Formula I encompasses all possible polymorphic modifications and other solid state modifications which possess the stated activity.

In the foregoing Formula I, various terms are defined in the following manner. The term $C_1$-$C_4$ straight or branched chain alkyl shall refer to, for example, methyl, ethyl, propyl, butyl, isopropyl, isobutyl, tertiary butyl and sec-butyl. The term $C_1$-$C_8$ straight or branched chain alkyl shall be inclusive of but not limited to such moieties as methyl, ethyl, propyl, isopropyl, butyl, isobutyl, sec-butyl, pentyl, neo-pentyl, hexyl, 3-methylpentyl, heptyl, 2-methylhexyl, octyl, 2-ethyhexyl but will not include the tertiary alkyl moiety. The term aryl shall refer to a phenyl group, and the term arylalkyl shall refer to a phenyl at the terminus of a $C_1$-$C_4$ straight carbon chain. The term optionally substituted shall refer to substitution on the phenyl ring and shall be of 1 to 3 in number and selected from $C_1$-$C_4$ straight chain alkoxy, chlorine, fluorine or bromine. The substitution on the phenyl ring may also be a mono 1-imidazolyl. The term heteroaryl is defined as a pyridyl optionally substituted by $C_1$-$C_4$ straight chain alkyl, thiophenyl or furyl.

The compounds which follow are some of those which serve to exemplify various aspects of the invention described herein.

a. N-[2-(4-Chlorophenyl)ethyl]-N'-[2-[1-[4-(1H-imidazol-1-yl)benzoyl]-4-piperidinyl]ethyl]-N'-methylthiourea.

b. N,N-Diethyl-N'-[[1-[4-(1H-imidazol-1-yl)benzoyl]-4-piperidinyl]methyl]guanidine.

c. N''-Cyano-N-ethyl-N'-[1-[4-(1H-imidazol-1-yl)benzoyl]-4-piperidinyl]-N-[[4-(1H-imidazol-1-yl)phenyl]methyl]guanidine.

d. 2-Butylamino-2-[[1-[4-(1H-imidazol-1-yl)benzoyl]-4-piperidinyl]amino]-1-nitroethene.

e. N-[3-(3,4-Dimethoxyphenyl)propyl]-N'-[1-[4-(1H-imidazol-1-yl)benzoyl]-4-piperidinyl]urea.

f. N-[1-[4-(1H-Imidazol-1-yl)benzoyl]-4-piperidinyl]-N'-(4-methylpentyl)urea.

g. N-Butyl-4-[4-(1H-imidazol-1-yl)benzoyl]-N-methyl-piperazine-1-carbothioamide.

h. N-(3-Chlorophenyl)-4-[4-(1H-imidazol-1-yl)benzoyl]-N'-methyl-N'-[2-(3,4,5-trimethoxyphenyl)ethyl]piperazine-1-carboximidamide.

i. N-Butyl-N'-cyano-N-ethyl-4-[4-(1H-imidazol-1-yl)benzoyl]piperazine-1-carboximidamide.

j. 4-[4-(1H-Imidazol-1-yl)benzoyl]piperazine-1-carboxylic acid butyl ester.

k. 1-[(5-Methyl-2-pyridinyl)carbonyl]-4-[4-(1H-imidazol-1-yl)benzoyl]piperazine.
l. N-[1-(1-Dipropylamino-2-nitroethenyl)-4-piperidinyl]-4-(1H-imidazol-1-yl)-N-methylbenzamide.
m. 4-[[4-(1H-Imidazol-1-yl)benzoyl](methyl)amino]-N,N,N'-tripropylpiperidine-1-carboximidamide.
n. N-[2-(4-Chlorophenyl)ethyl]-N'-cyano-4-[[4-(1H-imidazol-1-yl)benzoyl]amino]-N-methylpiperidine-1-carboximidamide.
o. 4-(1H-Imidazol-1-yl)-N-[1-(2-thienylcarbonyl)-4-piperidinyl]benzamide.

Process Aspect

In general the compounds of Formula I may be prepared as shown in Schemes A-F.

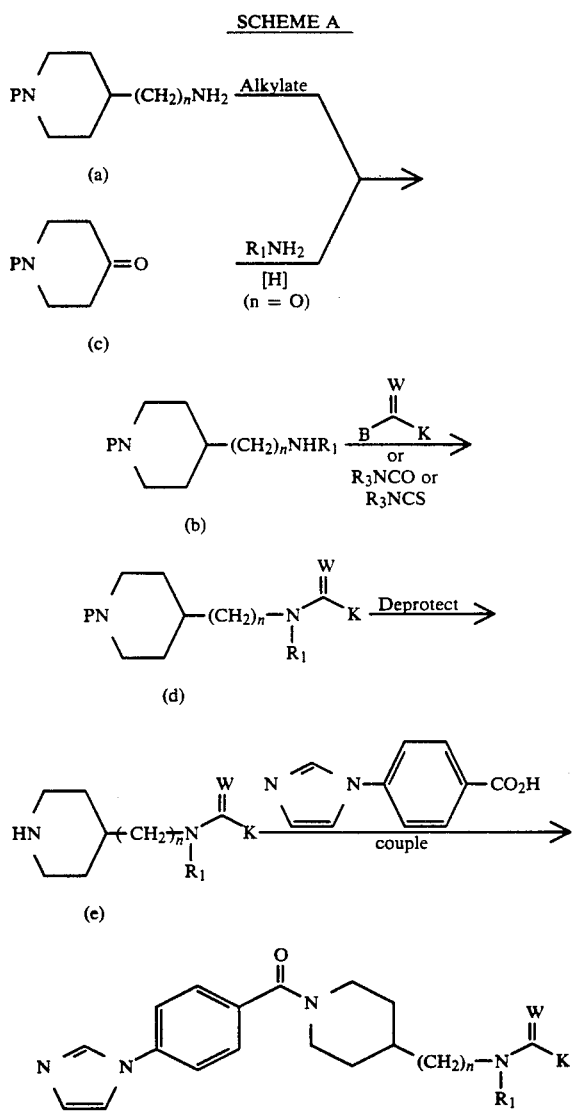

in Scheme A, P is a temporary protecting group for nitrogen such as benzyl, benzyloxycarbonyl, t-butoxycarbonyl, benzoyl, or acetyl; $R_1$ and $R_2$ are lower alkyl or hydrogen, $R_3$ is $C_1$-$C_8$ straight or branched chain alkyl, aryl, substituted aryl, aralkyl, substituted aralkyl or heteroaryl, with the proviso that $R_3$ is not tertiary alkyl; $R_4$ is loweralkyl or hydrogen; W is oxygen, sulfur, NR, NCN, or $CHNO_2$; K is $R_3$, $OR_3$, or $NR_2R_3$; B is a suitable leaving group such as chlorine, bromine, thiomethyl, thiophenyl, phenoxy, 1-imidazolyl and n=0-2.

The aminoalkylpiperidines (b) are conveniently prepared by alkylation of the primary amines (a). Typically, the amine (a) is treated with 1 to 2

The aminoalkylpiperidines (b) are conveniently prepared by alkylation of the primary amines (a). Typically, the amine (a) is treated with 1 to 2 equivalents of aldehyde or ketone in an organic solvent, most generally methanol, in the presence of molecular sieves. In some cases, it proves advantageous to add acid to the reaction mixture to maintain a slightly acidic pH. A reducing agent, most commonly sodium cyanoborohydride, is added to the mixture, and the reaction is stirred from 1 to 48 hr at temperatures from 0° C. to 40° C. The alkylated product (b) may be isolated by standard methods; for example, partitioning between organic and aqueous phases, standard chromatographic purification, and crystallization.

In some cases when n=0, it is preferable to prepare compounds (b) by reductive amination of the corresponding piperidones (c). The reductive amination is carried out in a fashion similar to that described above. Thus, the piperidone (c) and 0.5 to 1 equivalents of a primary amine are combined in an organic solvent such as methanol in the presence of molecular sieves, and optionally in the presence of added acid. A reducing agent such as sodium cyanoborohydride is added, and the reaction mixture is stirred from 1 to 48 hr at 0° C. to 40° C., after which standard procedures are used to isolate the product (b).

Reactions of amines (b) to give derivatized amines (d) follow methods appropriate to the specific derivatizing agent. In general, the amine (b) is treated with from 1 to 2 equivalents of the derivatizing reagent in an inert organic solvent, such as methylene chloride, acetonitrile, pyridine, or dimethylformamide, at temperatures from 0° C. to 100° C., for periods of from 0.5 to 48 hr. Some cases may be carried out advantageously in a two-phase mixture of an organic solvent and an aqueous solution of an inorganic base. The addition of 1 to 3 equivalents of a tertiary amine base is beneficial in some cases, as is the use of an inert atmosphere such as nitrogen. Products (d) are isolated by extractive workup, and are purified by standard crystallization or chromatographic methods.

Deprotection of the derivatized compounds (d) makes use of standard methodology appropriate for the protecting group. For example, when P is benzyl or benzyloxycarbonyl, deprotection may be accomplished by catalytic hydrogenolysis employing hydrogen gas at pressures of approximately 50 psi with a palladium catalyst in an alcoholic solvent at temperatures of 20° C. to 50° C. for 0.5 to 48 hr. When P is t-butoxycarbonyl, treatment of (d) with methanolic HCl at 0° C. to 20° C. for 1 to 5 hr effects deprotection. Standard isolation procedures may be used to obtain the deprotected product (e).

Coupling of the deprotected amines (e) with 4-(1H-imidazol-1-yl)benzoic acid may be accomplished using any standard amide forming method. For example, the benzoic acid may be combined with one equivalent of carbonyldiimidazole in a polar organic solvent such as dimethylformamide at approximately 20° for from 1 to 3 hr. The amine (e) is then added, and the mixture is stirred for 6 to 48 hr. The solvent is chromatography. In some cases it proves advantageous to isolate the products as their acid addition salts with a pharmaceutically acceptable acid such as methanesulfonic acid.

For some compounds of Formula I, it may prove advantageous to use synthetic steps as illustrated in Scheme B.

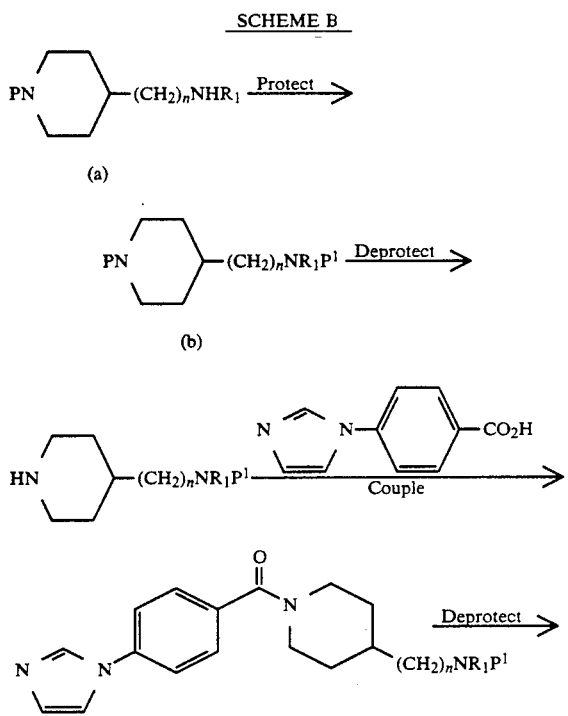

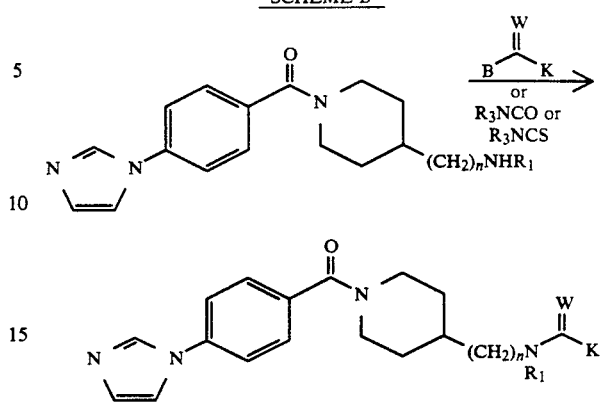

An amine (a), prepared as discussed previously, is protected with a protecting group $P^1$ which can be removed under conditions different from those used to remove P. For example, P can be benzyl and $P^1$ can be t-butoxycarbonyl. In this example, the amine (a) is dissolved in an alcoholic solvent such as methanol and 1.1 equivalents of di-t-butyldicarbonate is added. The mixture is stirred for from 15 min to 2 hr at temperatures from 20° C. to 70° C., after which the mixture is evaporated, and the crude product is purified by chromatography or crystallization. The process aspects for the remaining operations in Scheme B for the conversion of (b) to compounds of Formula I are generally the same as those described in connection with Scheme A.

Certain compounds of Formula I may be prepared conveniently by an alternative synthesis, shown in Scheme C.

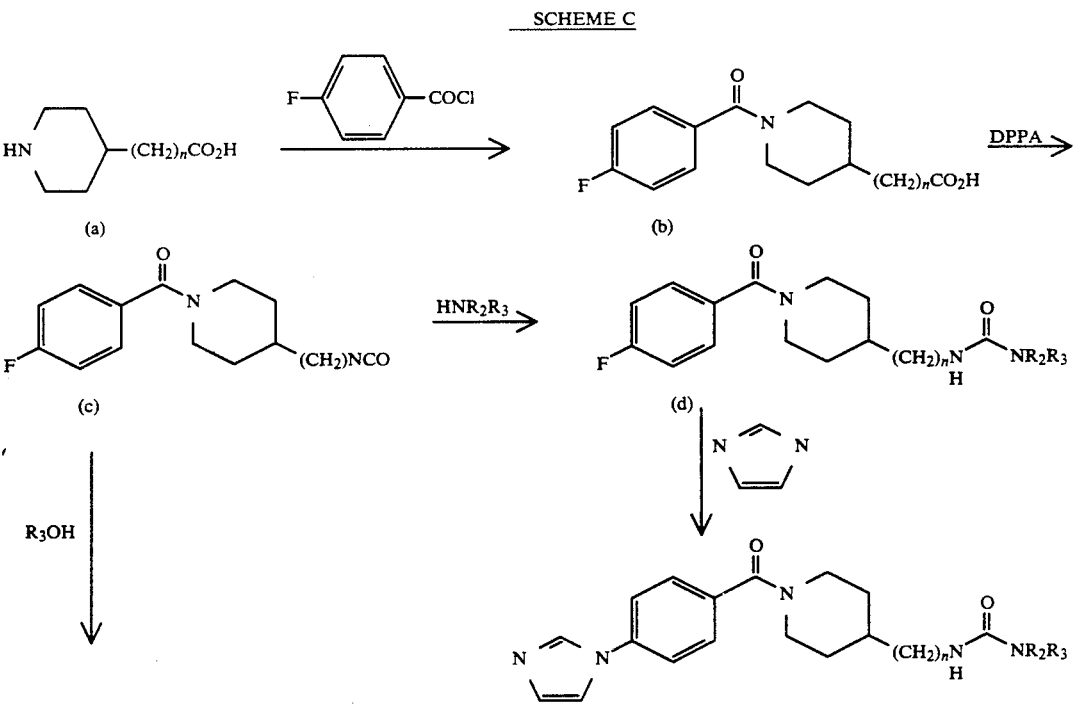

SCHEME C

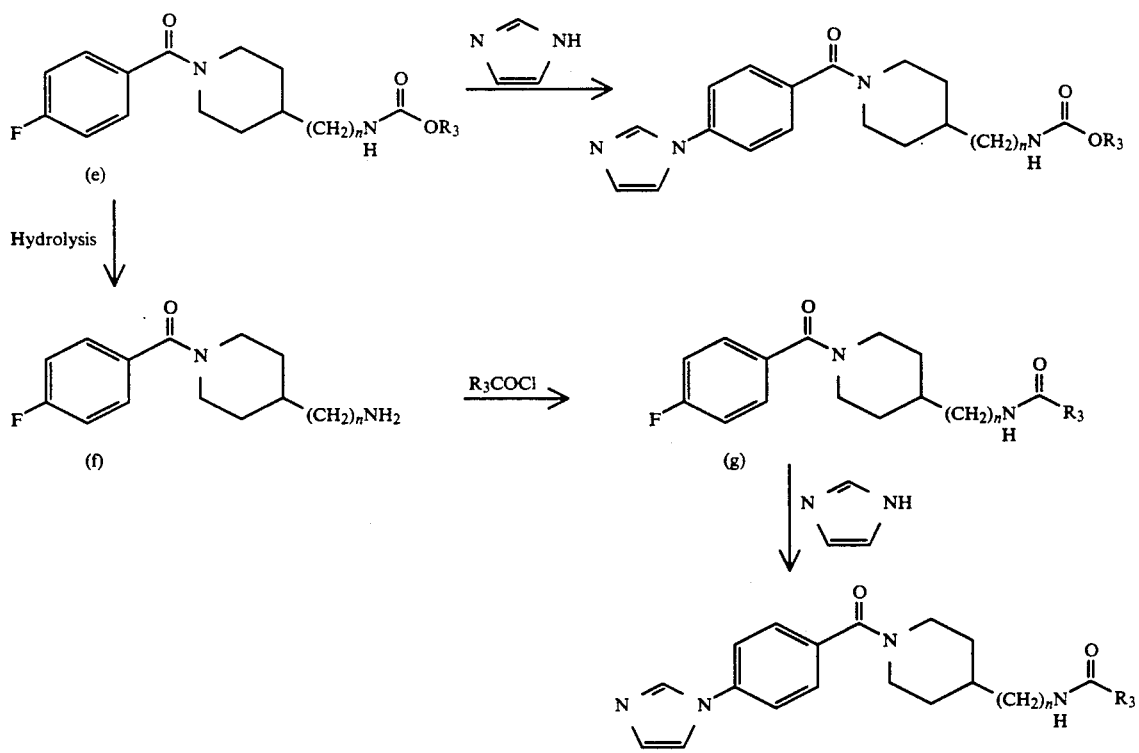

Piperidine (a) is acylated with 4-fluorobenzoyl chloride. The reactions are generally carried out in a mixture of a water-immiscible organic solvent such as methylene chloride and an aqueous solution of an inorganic base, for example, potassium carbonate. The acid chloride is added dropwise to the solution of the piperidine (a) over 10 min to 1 hr, typically at 0° C. to 10° C., after which stirring is continued at 0° C. to 25° C. for 30 min to 4 hr. The acylated products (b) may be isolated by acidification of the aqueous phase, extraction with an organic solvent, and recrystallization of the residue after evaporation.

Curtius rearrangement of the acids (b) gives the isocyanates (c). Most conveniently, the acid (b) is combined with one equivalent of diphenylphosphoryl azide (DPPA) and one equivalent of a tertiary amine base, typically triethylamine, in an inert solvent such as toluene. The mixture is heated at 75° C. to 100° C. under an inert atmosphere for 1 to 3 hr. The resulting solution of the isocyanate (c) is used without isolation. One to two equivalents of a primary or secondary amine may be added to the mixture, and the reaction continued at 20° C. to 80° C. for 1 to 6 hr to give the ureas (d). Alternatively, an alcohol may be reacted with the isocyanate in a similar fashion to give the carbamates (e). The products (d) and (e) may be isolated by washing the organic mixtures with aqueous acid and aqueous base, followed by evaporation of the organic phase. The crude products may be purified by standard crystallization or chromatographic methods.

Carbamates (e) may be converted to amines (f) using methodology appropriate to the specific group $R_3$. For example, within $R_3$ is benzyl, the removal may be accomplished by catalytic hydrogenolysis in the presence of hydrogen gas at pressures of about 50 psi with a palladium catalyst in an alcoholic solvent. The reactions are carried out at temperatures of 20° C. to 50° C. for 0.5 to 48 hr. When $R_3$ is 2-(trimethylsilyl)ethyl, the carbamate is combined with from 2 to 4 equivalents of cesium fluoride in a polar organic solvent, such as dimethylsulfoxide under an inert atmosphere, and the mixture is heated at 75° C. to 100° C. for from 2 to 8 hr. The product amines (f) may be isolated by extractive work-up followed by crystallization or chromatographic purification.

Amides (g) are prepared from the amines (f) using standard acylation methods. Typically, the amines are treated with acid chlorides in a mixture of a water-immiscible organic solvent and an aqueous inorganic base, as described previously. The products (g) are isolated by evaporation of the organic phase and recrystallization of the residue.

The fluorine in compounds (d), (e) and (g) may be displaced by imidazole to give the corresponding compounds of Formula I. The fluoro compounds are combined with from 3 to 6 equivalents of imidazole in a polar solvent such as acetonitrile, dimethylformamide, or dimethylsulfoxide, the latter being preferred. In most cases, addition of 1 to 3 equivalents of an inorganic base such as potassium carbonate is beneficial; however, this is not always necessary. The mixture is heated under an inert atmosphere at from 70° C. to 150° C. for 12 to 96 hr. The crude product may be isolated by extractive work-up; in some cases, the product may be precipitated by pouring the reaction mixture into water. The product is purified by recrystallization, in some cases as a pharmaceutically acceptable salt.

Compounds of Formula I in which Y is $CONR_2R_3$, $COR_3$, or $CHOHR_3$ are prepared as shown in Scheme D.

SCHEME D

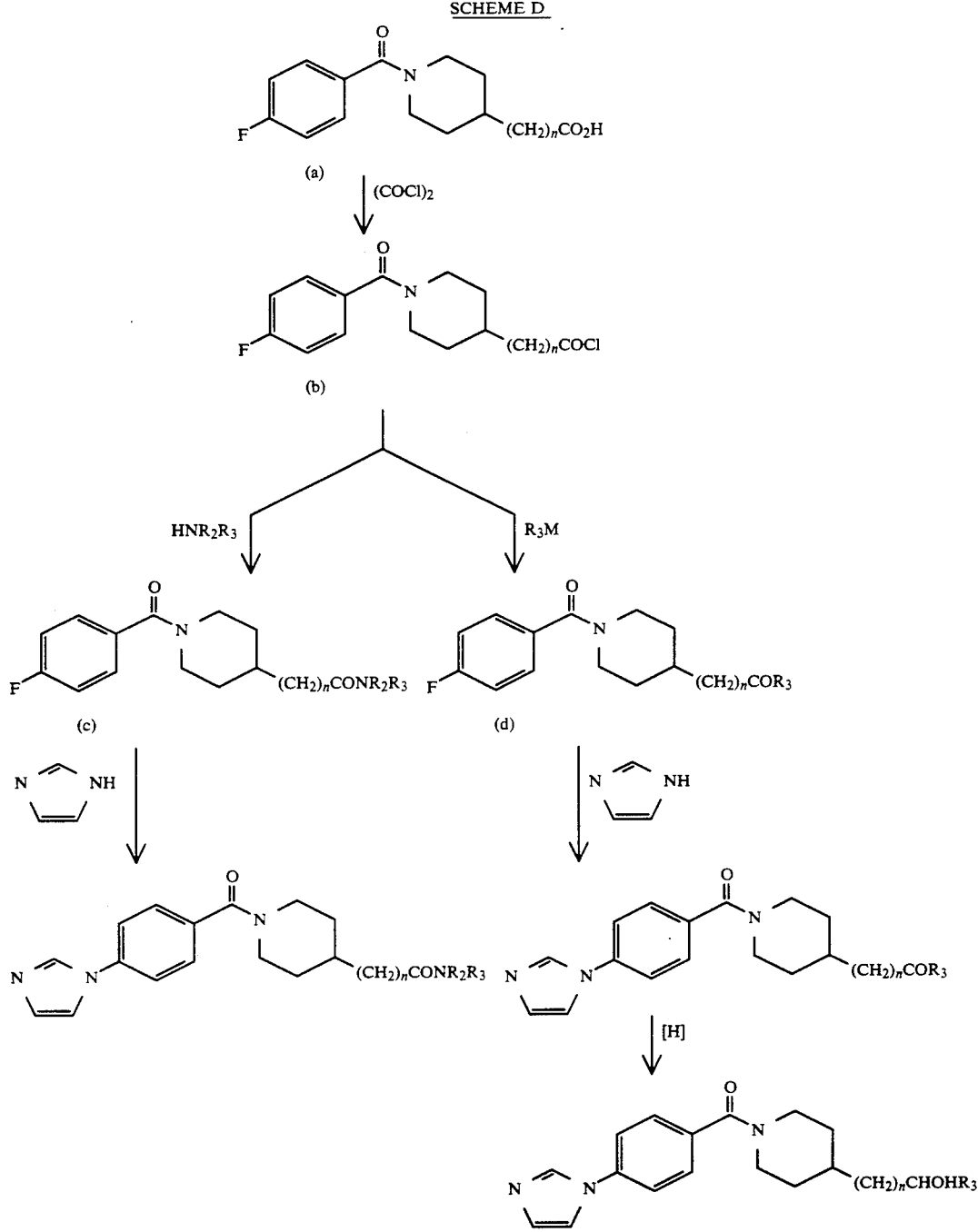

Carboxylic acid (a) is converted to its acid chloride (b) using thionyl chloride or oxalyl chloride, preferably the latter. For instance, the acid may be dissolved in an inert solvent such as methylene chloride and treated with 1.0 to 1.2 equivalents of oxalyl chloride at 0° C. to 25° C. Trace amounts of dimethylformamide are often useful to catalyze this reaction. The mixture is stirred for from 1 to 4 hr. Evaporation of the solvent provides the crude acid chloride, which may be used without further purification.

Preparation of amides (c) is accomplished by treatment of the acid chloride (b) with an amine, using standard amide forming reaction conditions, most preferably those involving a two-phase organic solvent and aqueous inorganic base mixture. Compound (c) may then be converted to the corresponding compounds of Formula I by reaction with imidazole, as previously discussed.

Conversion of the acid chloride (b) to ketones (d) is best accomplished by reaction with an organometallic reagent ($R_3M$), for example, by organocadmium, organocuprate, or copper catalyzed Grignard addition. Most commonly, an organocopper reagent is prepared by reaction of copper (I) iodide with one equivalent of methyllithium in a solvent such as tetrahydrofuran under an inert atmosphere from −80° C. to 20° C. for 1 hr. The mixture is cooled to −80° C., a Gringnard regent $(R_3)MgX$ is added, and the mixture is stirred from $-80°$ C. to $20°$ C. for 1 to 2 hr. The mixture is once more cooled to $-80°$ C., and a solution of the acid chloride (b) is added dropwise over approximately 30 min. The mixture is then stirred 1 hr at $-80°$ C., 2 to 4 hr at $20°$ C., and is quenched with aqueous ammonium chloride. Isolation of the product ketone (d) involves partitioning between an organic solvent and aqueous base. At times small amounts of methyl ketone (i.e., $R_3$=methyl) may be obtained as impurities in (d). These may be removed by standard chromatographic or crystallization methods.

Compounds (d) may be converted to the corresponding compounds of Formula I by reaction with imidazole, as previously discussed. Keto compounds of Formula I may be reduced by a metal hydride reagent in an appropriate solvent, preferably by sodium borohydride in an alcoholic solvent such as methanol. These reductions are best carried out by treating a solution of the ketone at $0°$ C. to $20°$ C. with 0.5 to 2 equivalents of sodium borohydride for from 30 min to 5 hr. The crude product is obtained by aqueous workup, and purification is effected by crystallization.

Certain compounds of Formula I are most conveniently prepared as shown in Scheme E.

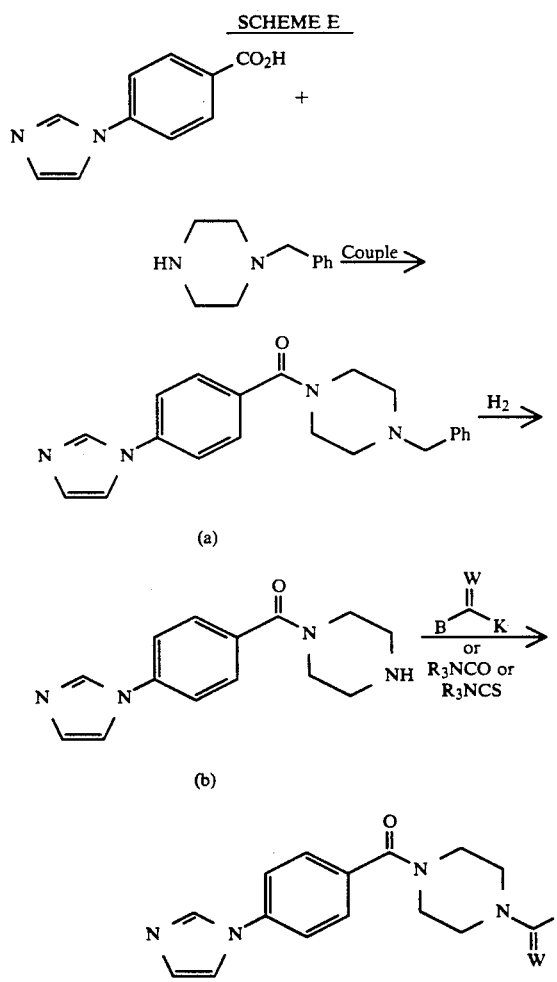

The process aspects of this preparation are generally similar to those described in connection with Scheme B. Thus, 4-(1H-imidazol-1-yl)benzoic acid is coupled with 1-benzylpiperazine to give amine (a), which is converted to the debenzylated amine (b) by catalytic hydrogenolysis. Derivatization on nitrogen with the appropriate reagents leads to compounds of Formula I. Similarly, other compounds of Formula I may be prepared in an analogous fashion, as shown in Scheme F.

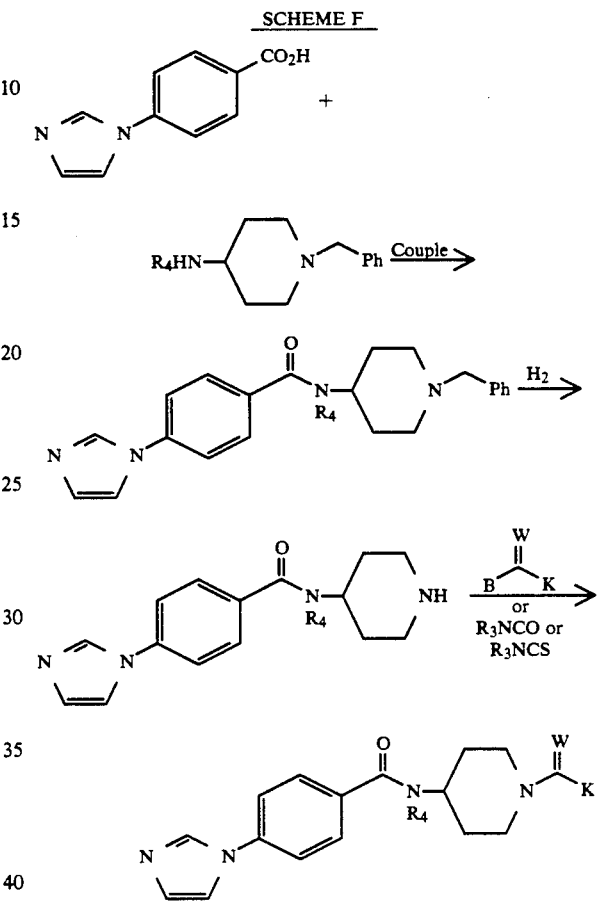

METHOD-OF-USE AND PHARMACEUTICAL COMPOSITION ASPECTS

The novel imidazolylbenzoyl substituted heterocycles of this invention and their pharmaceutically acceptable salts are antiarrhythmic agents primarily with a Class III antiarrhythmic effect. Certain of the compounds also exhibit a Class I antiarrhythmic effect.

In 1970, Vaughan Williams devised his, by now well known, method for classifying various antiarrhythmic agents. Generally speaking, Class I agents typified for example by flecainide, lidocaine or mexiletine are local anesthetics on nerve and myocardial membranes thereby slowing conduction, which decreases the propagation of ectopic (premature) beats and suppresses the tendency of damaged cells to initiate ectopic beats. The Class II agents are the so-called $\beta$-blockers best exemplified by propranolol. The Class III agents represented by bretylium or amiodarone have little or no effect on conduction; in fact, they are quite independent of conduction. They prolong the action potential duration of the heart cells thus increasing the time interval in which the heart cells are unexcitable (refractory period) without slowing conduction or changing the excitability of the cardiac cells.

The compounds of this invention were tested in several biological procedures to analyze their type of antiarrhythmic effect. For instance, utilizing standard electrophysiological techniques, the resting potential, amplitude, duration and rate of rise of phase 0 (depolarization) of the action potential were measured in normal canine cardiac Purkinje fibers. Those compounds which in this screen demonstrated an increase in action potential duration without a decrease in the rate of rise of phase 0 were designated Class III antiarrhythmic agents. Those compounds which decreased the rate of rise of phase 0 i.e. slowed conduction were designated as Class I agents.

Certain compounds were tested for their vasodilator activity—such compounds would be useful for the treatment of hypertension or heart failure. The compounds were evaluated by assessing vasodilator activity in rings of canine coronary artery and mesenteric vein in vitro.

In general, the compounds of this invention may be administered orally or parenterally. The dosage administered will be dependent on the subject being treated, the route of administration and the type and severity of the arrhythmias being prevented or reduced.

The compound to be administed can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. For parenteral administration a compound of this invention can be formulated as an intramuscular or intravenous medicament but is not limited thereto. In the case of treatment of a patient suffering from severe cardiac arrhythmias, it may be desirable to administer a compound of this invention by an intravenous slow bolus in order to effect a rapid conversion to a normal sinus rhythm. The normalized condition can then be maintained by oral administration of the compound.

The compounds of this invention can be formulated for parenteral administration with any of a number of pharmaceutically acceptable carriers and diluents to constitute an injectable liquid solution. Commonly used diluents and carriers include water or a saline solution, buffered aqueous solutions as well as dispersing and surface active agents if necessary. Such formulations can be infused at a constant rate or injected one to four times per day or more often depending upon the particular condition of the subject being treated.

It is further contemplated that the compounds of this invention may be formulated into sublingual lozenges or impregnated into fabric appliques for a type of transdermal application.

The pharmaceutical formulations of the compounds of this invention may optionally, additionally contain one or more other pharmaceutically active substances, as for instance combining the compounds of this invention with β-adrenergic blocking agents for the treatment of mammalian subjects who have suffered myocardial infarction.

The invention described hereinabove is illustrated below in the Preparations and Examples, which, however, are not to be construed as limiting the scope of this invention.

PREPARATIONS

Preparation 1

1-(4-Fluorobenzoyl)piperidine-4-carboxylic acid

Piperidine-4-carboxylic acid (25.8 g, 200 mmol) and potassium carbonate (82.9 g, 600 mmol) are combined in water (500 mL) and methylene chloride (1 L) at 0° C. 4-Fluorobenzoyl chloride (31.7 g, 200 mmol) is dissolved in methylene chloride (200 mL) and added to the first mixture dropwise over 45 min. The mixture is stirred for 2 hr, after which the aqueous layer is separated and acidified to pH 1.5 with concentrated HCl. The aqueous mixture is extracted three times with methylene chloride, and the organic extracts are dried over magnesium sulfate and evaporated to give the title compound.

NMR (CDCl$_3$): δ=1.73(br s,2), 1.97(br s,2), 2.63(m,1), 3.09(br t,2), 3.73(br s,1), 4.48(br s,1), 7.10(t,2), 7.41(m,2).

Preparation 2

In a manner similar to that described in Preparation 1, treat the following reactants, respectively:
a) 1-(4-Fluorobenzoyl)-4-piperidinamine and hexanoyl chloride,
b) Piperidine-4-carboxylic acid and benzyl chloroformate, to obtain the following products, respectively:
c) N-[1-(4-Fluorobenzoyl)-4-piperidinyl]hexanamide,
d) 1-[(Phenylmethoxy)carbonyl]piperidine-4-carboxylic acid.

Preparation 3

N-Butyl-1-(4-fluorobenzoyl)piperidine-4-carboxamide 1-(4-Fluorobenzoyl)piperidine-4-carboxylic acid (8.79 g, 35.0 mmol) is dissolved in methylene chloride (75 mL) at 0° C., and dimethylformamide (0.20 mL) and oxalyl chloride (4.9 g, 39 mmol) are added. The mixture is stirred at room temperature for 2 hr. In a second flask, butylamine (2.6 g, 35 mmol) and potassium carbonate (9.67 g, 75.4 mmol) are dissolved in water (100 mL) and methylene chloride (200 mL) at 0° C. The first mixture is added to the second dropwise over 45 min, and the mixture is stirred at 0° C. for 2 hr. The organic phase is separated, washed twice with saturated sodium bicarbonate, twice with 1N HCl, dried over magnesium sulfate, and evaporated. Recrystallization from ethyl acetate-hexane affords the title compound.

NMR (CDCl$_3$): δ=0.93(t,3), 1.31(sextuplet,2), 1.49(quint,2), 1.76(m,4), 2.30(m,1), 2.93(m,2), 3.26(quar,2), 3.79(m,1), 4.63(m,1), 5.48(m,1), 7.09(t,2), 7.41(dd,2).

Preparation 4

1-(4-Fluorobenzoyl)-4-(2-oxohexyl)piperidine 1-(4-Fluorobenzoyl)piperidine-4-carboxylic acid (11.31 g, 45.0 mmol) is dissolved in methylene chloride (100 mL) at 0° C., and dimethylformamide (0.20 mL) and oxalyl chloride (5.8 g, 46 mmol) are added. The mixture is stirred 3 hr at room temperature, after which the solvent is evaporated; toluene (50 mL) is added and evaporated under reduced pressure. The toluene treatment is then repeated. In a second flask, copper (I) iodide (8.57 g, 45.0 mmol) is suspended in tetrahydrofuran (100 mL) at −78° C. under a nitrogen atmosphere. Methyllithium (1.55M in ether, 29 mL, 45 mmol) is added, and the mixture is stirred at room temperature for 50 min. The mixture is cooled to −78° C., and pentylmagnesium bromide (2.0M in ether, 22.5 mL, 45 mmol) is added. The mixture is stirred for 15 min at −78° C., 1.5 hr at room temperature, and is cooled to −78° C. A solution of the first residue in tetrahydrofuran (30 mL) is added to the second mixture dropwise over 30 min, and the mixture is stirred 1 hr at −78° C., and then 3 hr at room temperature. The mixture is poured into saturated ammonium chloride (500 mL), sodium hydroxide (1 g) is added, and the mixture is stirred 16 hr. The layers are separated, the aqueous phase is extracted twice with methylene chloride, and the combined organics are washed twice with 1N sodium hydroxide, once with brine, dried over magnesium sulfate, and evaporated. The residue is chromatographed on silica gel eluting with hexane and ethyl acetate mixtures and recrystallized from ether-petroleum ether to afford the title compound.

NMR (CDCl$_3$): δ=0.89(t,3), 1.28(m,4), 1.58(m,4), 1.85(br s,2), 2.47(t,2), 2.60(m,1), 2.99(br s,2), 3.79(br s,1), 4.57(br s,1), 7.09(t,2), 7.40(dd,2).

Preparation 5

1-(4-Fluorobenzoyl)-4-(1-oxoethyl)piperidine

In a manner similar to that described in Preparation 4, 1-(4-fluorobenzoyl)piperidine-4-carboxylic acid is reacted with methylmagnesium bromide to afford the title compound.

NMR (CDCl$_3$): δ=1.64(m,2), 1.88(m,2), 2.20(s,3), 2.62(m,1), 3.01(br s,2), 3.73(br s,1), 4.54(br s,1), 7.11(t,2), 7.41(m,2).

Preparation 6

[1-(4-Fluorobenzoyl)-4-piperidinyl]carbamic acid, 2-(trimethylsilyl)ethyl ester 1-(4-Fluorobenzoyl)piperidine-4-carboxylic acid (10.05 g, 40.0 mmol) and triethylamine (4.1 g, 40 mmol) are combined in toluene (50 mL) under a nitrogen atmosphere. Diphenylphosphoryl azide (11.0 g, 40.0 mmol) is added, and the mixture is heated at 80° C. for 2 hr. 2-(Trimethylsilyl)ethanol (9.49 g, 80.2 mmol) is added, and the mixture is stirred at 80° C. for 2 hr, and room temperature for 2 hr. The mixture is diluted with methylene chloride, washed twice with 1N HCl, twice with 0.5N sodium hydroxide, dried over magnesium sulfate, and evaporated. The residue is recrystallized from ether-hexane to afford the title compound.

NMR (CDCl$_3$): δ=0.04(s,9), 0.98(m,2), 1.31(m,2), 1.91(m,2), 2.99(m,2), 3.67(m,2), 4.15(m,2), 4.59(m,2), 7.11(t,2), 7.42(dd,2).

Preparation 7

4-[[(Butoxy)carbonyl]amino]piperidine-1-carboxylic acid, phenylmethyl ester

In a manner similar to that described in Preparation 6, 1-[(phenylmethoxy)carbonyl]piperidine-4-carboxylic acid and 1-butanol are reacted to give the title compound.

Preparation 8

1-(4-Fluorobenzoyl)-4-piperidinamine hydrochloride

[[1-(4-Fluorobenzoyl)-4-piperidinyl]]carbamic acid 2-(trimethylsilyl)ethyl ester (14.66 g, 40.0 mmol) and cesium fluoride (12.14 g, 79.9 mmol) are combined in dimethyl sulfoxide (100 mL) under a nitrogen atmosphere and heated to 80° C. for 4 hr. The mixture is poured onto water (1 L) and extracted three times with methylene chloride. The organic extracts are dried over magnesium sulfate and evaporated to provide the title compound as its free base. The material is converted to its hydrochloride salt and recrystallized from 2-propanol-ether to provide the title compound.

NMR (DMSO-d$_6$): δ=1.49(m,2), 1.94(br s,2), 2.84-3.19(m,2), 3.33(m,1), 3.61(br s,1), 4.42(br s,1), 7.30(t,2), 7.60(dd,2), 8.27(br,3).

Preparation 9

N-Methyl-1-(phenylmethyl)-4-piperidinamine dihydrochloride 1-(Phenylmethyl)-4-piperidone (18.99 g, 100 mmol), methylamine hydrochloride (6.75 g, 100 mmol), and 3 Å molecular sieves (54 g) are combined in methanol (350 mL), and the mixture is stirred 2 hr. Acetic acid (2 mL) and sodium cyanoborohydride (4.19 g, 66.7 mmol) are added, and the mixture is stirred for 48 hr at room temperature. The mixture is filtered through Celite, diluted with 1N sodium hydroxide, and extracted three times with methylene chloride. The organic extracts are dried over magnesium sulfate and evaporated to give the title compounds as its free base. The material is converted to its hydrochloride salt and recrystallized from methanol-ether to give the title compound.

NMR (DMSO-d$_6$): δ=2.05(m,2), 2.25(m,2), 3.00(m,2), 3.18(m,1), 3.40(m,5), 4.29(br s,2), 7.48(m,3), 7.63(m,2), 9.47(br s,2), 11.18(br s,1).

Preparation 10

N-Butyl-N'-[1-(phenylmethyl)-4-piperidinyl]urea

Butyl isocyanate (33.9 g, 342 mmol) is added dropwise to a solution of 1-(phenylmethyl)-4-piperidinamine (65 g, 342 mmol) in methylene chloride (400 mL) at 0° C., and the mixture is stirred for 2 hr. The mixture is washed three times with water, dried over magnesium sulfate, and evaporated. Recrystallization of the residue from methylene chloride-hexane affords the title compound.

NMR (CDCl$_3$): δ=0.91(t,3), 1.3-1.6(m,6), 1.91(m,2), 2.1(dt,2), 2.8(d,2), 3.13(quar,2), 3.48(s,2), 3.60(m,1), 4.35(d,1), 4.45(t,1), 7.20-7.50(m,5).

Preparation 11

N-Butyl-N'-methyl-N'-[1-(phenylmethyl)-4-piperidinyl]urea hydrochloride

In a manner similar to that described in Preparation 10, butyl isocyanate is reacted with N-methyl-1-(phenylmethyl)-4-piperidinamine to afford the title compound.

NMR (DMSO-d$_6$): δ=0.88(t,3), 1.26(sextet,2), 1.39(quin,2), 1.62(br d,2), 2.12(br quar,2), 2.64(s,3), 3.02(m,4), 3.31(m,2), 4.28(m,3), 6.32(t,1), 7.48(m,3), 7.65(m,2), 10.96(br s,1).

Preparation 12

[1-(Phenylmethyl)-4-piperidinyl]carbamic acid, 1,1-dimethylethyl ester 1-(Phenylmethyl)-4-piperidinamine (78 g, 410 mmol) is dissolved in methanol (400 mL) and di-tert-butyl dicarbonate (95 g, 440 mmol) is added over 5 min. The solution is stirred 15 min at room temperature, 20 min at 70° C., and then evaporated. Trituration of the residue with ether affords the title compound.

NMR (CDCl$_3$): δ=1.44(m,11), 1.88(m,2), 2.08(t,2), 2.78(m,2), 3.48(m,3), 4.42(br s,1), 7.31(m,5).

Preparation 13

1-[4-(1H-Imidazol-1-yl)benzoyl]-4-(phenylmethyl)piperazine methanesulfonic acid salt (1:2)

4-(1H-Imidazol-1-yl)benzoic acid (18.82 g, 100 mmol) and carbonyldiimidazole (16.22 g, 100 mmol) are combined in dimethylformamide (200 mL) and stirred for 2 hr. 1-(Phenylmethyl)piperazine (17.7 g, 101 mmol) is added, and the mixture is stirred for 20 hr. The solvent is evaporated, and the residue is dissolved in methylene chloride and washed twice with saturated aqueous sodium bicarbonate, twice with water, and dried over magnesium sulfate. Evaporation of the solvent and recrystallization of the residue from ethyl acetate-hexane provides the free base of the title compound. Conversion to the methanesulfonic acid salt and recrystallization from ethanol-ether affords the title compound.

NMR (DMSO-d$_6$): δ=2.37(s,6), 3.01–3.88(br m,8), 4.39(s,2), 7.50(m,3), 7.55(m,2), 7.74(d,2), 7.95(m,3), 8.35(s,1), 9.73(s,1).

Preparation 14

In a manner similar to that described in Preparation 13, 4-(1H-imidazol-1-yl)benzoic acid is reacted with the following reactants, respectively:
a) (4-Piperidinyl)carbamic acid, 1,1-dimethylethyl ester,
b) 1-(Phenylmethyl)-4-piperidinamine, to provide the following products, respectively:
c) [1-[4-(1H-Imidazol-1-yl)benzoyl]-4-piperidinyl]carbamic acid, 1,1-dimethylethyl ester,
d) 4-(1H-Imidazol-1-yl)-N-[1-(phenylmethyl)-4-piperidinyl]benzamide.

Preparation 15

1-[4-(1H-Imidazol-1-yl)benzoyl]piperazine

1-[4-(1H-Imidazol-1-yl)benzoyl]-4-(phenylmethyl)piperazine (26.65 g, 76.9 mmol) is dissolved in ethanol (500 mL) and 10% palladium on carbon (2.00 g) as a slurry in water (10 mL) is added to the solution. The mixture is shaken under an atmosphere of hydrogen on a Parr apparatus at 50 psi and 50° C. for 30 hr. The mixture is filtered through Celite, the solvent is evaporated, and the residue is triturated with ether and crystallized from ethyl acetate-hexane to afford the title compound.

NMR (CDCl$_3$): δ=1.76(br s,1), 2.90(br m,4), 3.43(br s,2), 3.76(br s,2), 7.23(s,1), 7.31(s,1), 7.45(d,2), 7.55(d,2), 7.89(s,1).

Preparation 16

In a manner similar to that described in Preparation 15, the following reactants, respectively:
a) [1-(Phenylmethyl)-4-piperidinyl]carbamic acid, 1,1-dimethylethyl ester,
b) 4-(1H-Imidazol-1-yl)-N-[1-(phenylmethyl)-4-piperidinyl]benzamide,
c) N-Butyl-N'-methyl-N'-[1-(phenylmethyl)-4-piperidinyl]urea hydrochloride,
d) N-Butyl-N'-[1-(phenylmethyl)-4-piperidinyl]urea,
e) 4[[(Butoxy)carbonyl]amino]piperidine-1-carboxylic acid, phenylmethyl ester.
are converted to the following products, respectively:
f) (4-Piperidinyl)carbamic acid, 1,1-dimethylethyl ester,
g) 4-(1H-Imidazol-1yl)-N-(4-piperidinyl)benzamide,
h) N-Butyl-N'-methyl-N'-(4-piperidinyl)urea hydrochloride,
i) N-Butyl-N'-(4-piperidinyl)urea,
j) (4-Piperidinyl)carbamic acid, butyl ester.

Preparation 17

1-[4-(1H-Imidazol-1-yl)benzoyl]-4-piperidinamine dihydrochloride

[1-(4-(1H-Imidazol-1-yl)benzoyl]-4-piperidinyl]carbamic acid, 1,1-dimethylethyl ester (131.6 g, 355 mmol) is dissolved in methanol (800 mL) at 0° C., and the solution is saturated with HCl gas. The mixture is stirred for 3 hr at room temperature, after which ether is added to give a turbid solution. The resulting precipitate is collected and air dried to afford the title compound.

NMR (DMSO-d$_6$): δ 1.63(m,2), 1.97(m,1), 2.06(m,1), 2.96(m,1), 3.21(m,1), 3.33(m,2), 3.60(m,1), 4.50(m,1), 7.65(d,2), 7.96(s,1), 7.97(d,2), 8.39(s,1), 8.57(br s,3), 9.85(s,1).

EXAMPLES

Example 1

N-[1-[4-(1H-Imidazol-1-yl)benzoyl]-4-piperidinyl]hexanamide

N-[1-(4-Fluorobenzoyl)-4-piperidinyl]hexanamide (5.73 g, 17.9 mmol) imidazole (6.09 g, 89.5 mmol), and potassium carbonate (4.59 g, 35.8 mmol) are combined in dimethylsulfoxide (75 mL) under a nitrogen atmosphere, and the mixture is heated at 130° C. for 42 hr. The mixture is cooled, poured on water, and extracted with methylene chloride. The extracts are washed with brine, dried over magnesium sulfate, and evaporated. Recrystallization of the residue from ethyl acetate provides the title compound.

NMR (CDCl$_3$): δ=0.89(t,3), 1.31(m,6), 1.61(quin,2), 2.00(m,2), 2.16(t,2), 2.96(m,1), 3.73(m,1), 4.63(m,1), 5.45(d,1), 7.24(s,1), 7.31(s,1), 7.45(d,2), 7.90(s,1).

Example 2

In a manner similar to that described in Example 1, the following reactants, respectively:
a) N-Butyl-1-(4-fluorobenzoyl)piperidine-4-carboxamide,
b) 1-(4-Fluorobenzoyl)-4-(1-oxohexyl)piperidine,
c) 1-(4-Fluorobenzoyl)-4-(1-oxoethyl)piperidine,
are converted to the following products, respectively:
d) N-Butyl-1-[4-(1H-imidazol-1-yl)benzoyl]piperidine-4-carboxamide, methanesulfonic acid salt,
e) 1-[4-(1H-Imidazol-1-yl)benzoyl]-4-(1-oxohexyl)piperidine,
f) 1-[4-(1H-Imidazol-1-yl)benzoyl]-4-(1-oxoethyl)piperidine hydrochloride.

EXAMPLE 3

4-(1-Hydroxyhexyl)-1-[4-(1H-imidazol-1-yl)benzoyl]piperidine, methanesulfonic acid salt 1-[4-(1H-Imidazol-1-yl)benzoyl]-4-(1-oxohexyl)piperidine (0.67 g, 1.90 mmol) is dissolved in methanol (10 mL) at 0° C., and sodium borohydride (72 mg, 1.9 mmol) is added. The mixture is stirred for 3 hr at 0° C., after which it is diluted with water and made acidic with 2N HCl. The solution is washed three times with methylene chloride, made basic with sodium carbonate, and extracted with methylene chloride. The extracts are dried with magnesium sulfate and evaporated to a residue. Recrystallization of the product as its methanesulfonic acid salt from ethanol-ether provides the title compound.

NMR (DMSO-d$_6$): $\delta$=0.87(t,3), 1.10–1.88(m,13), 2.24(s,3), 2.72(br s,1), 3.01(br s,1), 3.21(br s,1), 3.52(br m,1), 4.54(br m,1), 7.64(d,2), 7.89(d,2), 7.94(s,1), 8.34(s,1), 9.71(s,1).

Example 4

N-Butyl-N'-[1-[4-(1H-imidazol-1-yl)benzoyl]-4-piperidinyl]N'-methylurea methanesulfonic acid salt 4-(1H-Imidazol-1-yl)benzoic acid (4.52 g, 24.0 mmol) and carbonyldiimidazole (3.89 g, 24.0 mmol) are combined in dimethylformamide (50 mL) and the mixture is stirred 2 hr. A solution of N-butyl-N'-methyl-N'-(4-piperidinyl)urea (6.00 g, 24.0 mmol) in dimethylformamide (25 mL) is added, and the mixture is stirred 18 hr. The solvent is removed by evaporation and the residue is dissolved in methylene chloride. The solution is washed twice with saturated aqueous sodium bicarbonate and twice with water, dried over magnesium sulfate, and evaporated to a residue. Recrystallization of the crude product as its methanesulfonic acid salt from ethanol-ether provides the title compound.

NMR (DMSO-d$_6$): $\delta$=0.87(t,3), 1.25(sextet,2), 1.37(quin,2), 1.61(br s,4), 2.35(s,3), 2.66(s,3), 2.84(br m,1), 3.01(m,2), (br m,1), 3.01(m,2), 3.13(br m,1), 3.55(br m,1), 4.21(br m,1), 4.57(br m,1), 6.27(br s,1), 7.70(d,2), 7.90(d,2), 7.95(s,1), 8.35(s,1), 9.73(s,1).

Example 5

N-[1-[4-(1H-Imidazol-1-yl)benzoyl]-4-piperidinyl]-3-pyridinecarboxamide

In a manner similar to that described in Example 4, nicotinic acid and 1-[4-(1H-imidazol-1-yl)benzoyl]-4-piperidinamine are converted to the title compound.

Example 6

N-Butyl-N'-[1-[4-(1H-Imidazol-1-yl)benzoyl]-4-piperidinyl]urea methanesulfonic acid salt 4-(1H-Imidazol-1-yl)benzoic acid (2.6 g, 13.9 mmol), toluene (35 mL), and thionyl chloride (35 mL) are combined and heated at 70° C. for 1.5 hr, after which the mixture is evaporated. The residue is combined with N-butyl-N'-(4-piperidinyl)urea (2.0 g, 10 mmol) in methylene chloride (40 mL) at −78° C. under a nitrogen atmosphere, and triethylamine (4 mL) in methylene chloride (10 mL) is added dropwise. The mixture is allowed to warm to room temperature and is stirred for three days. The mixture is evaporated to a residue which is triturated with ethanol. The ethanol is evaporated, and the residue is chromatographed on silica. The chromatographed material is converted to its methanesulfonic acid salt and recrystallized from isopropanol-acetonitrile to yield the title compound.

NMR (DMSO-d$_6$): $\delta$=0.84(t,3), 1.30(m,6), 1.74–1.84(br,1), 2.32(s,3), 2.96(t,3), 3.00–3.90(br,13), 4.28(br,1), 5.80–5.84(br,2), 7.68(d,2), 7.90(d,2), 7.93(s,1), 8.34(s,1), 9.68(s,1).

Example 7

[1-[4-(1H-Imidazol-1-yl)benzoyl]-4-piperidinyl]carbamic acid butyl ester, methanesulfonic acid salt In a manner similar to that described in Example 6, 4-(1H-imidazol-1-yl)benzoic acid and (4-piperidinyl)carbamic acid, butyl ester are reacted to give the title compound.

Example 8

N-Butyl-N'-[1-[4-(1H-Imidazol-1-yl)benzoyl]-4-piperidinyl]thiourea

1-[4-(1H-Imidazol-1-yl)benzoyl]-4-piperidinamine (4.06 g, 15.0 mmol) and butyl isothiocyanate (1.81 mL, 1.73 g, 15.0 mmol) are combined in methylene chloride (75 mL) and stirred at room temperature. After 24 hr, an additional portion (0.90 mL, 0.86 g, 7.5 mmol) of butyl isothiocyanate is added, and the mixture is stirred for 48 hr. The mixture is washed twice with 1N aqueous sodium hydroxide, once with brine, dried over magnesium sulfate, and evaporated. Trituration of the residue with ether and recrystallization from ethanol-ether affords the title compound.

NMR (DMSO-d$_6$): $\delta$=0.89(t,3), 1.31(m,2), 1.46(m,4), 1.91(br s,2), 3.00(br s,1), 3.13(br s,1), 3.40(br s,2), 3.60(br s,1), 4.33(br s,2), 7.15(s,1), 7.32(br m,2), 7.54(d,2), 7.76(d,2), 7.83(s,1), 8.36(s,1).

Example 9

In a manner similar to that described in Example 8, the following reactants, respectively:
a) 1-[4-(1H-Imidazol-1-yl)benzoyl]piperazine,
b) N-(4-Piperidinyl)-4-(1H-imidazol-1-yl)benzamide, are reacted with butyl isocyanate to give the following products, respectively:
c) N-Butyl-4-[4-(1H-imidazol-1-yl)benzoyl]piperazine-1-carboxamide,
d) N-Butyl-4-[[4-(1H-imidazol-1-yl)benzoyl]amino]-piperidine-1-carboxamide.

Example 10

N-[1-[4-(1H-Imidazol-1-yl)benzoyl]-4-piperidinyl]benzenepropanamide

1-[4-(1H-Imidazol-1-yl)benzoyl]-4-piperidinamine dihydrochloride (4.46 g, 13.0 mmol) and potassium carbonate (6.67 g, 52.0 mmol) are dissolved in methylene chloride (60 mL) and water (30 mL) and the mixture is cooled with an ice bath. A solution of 3-phenylpropionyl chloride (2.72 g, 16.2 mmol) in methylene chloride (15 mL) is added dropwise over 15 min, and the mixture is stirred at room temperature for 2 hr. The phases are separated, and the organic phase is washed with saturated aqueous sodium bicarbonate, dried over magnesium sulfate, and evaporated. Chromatography of the residue on silica gel followed by recrystallization from acetonitrile affords the title compound.

NMR (DMSO-d$_6$): $\delta$=1.30(br s,2), 1.74(br s,2), 2.37(t,2), 2.82(t,2), 3.10(br s,2), 3.55(br s,1), 3.82(br m,1), 4.27(br s,1), 7.14(s,1), 7.17–7.29(m,5), 7.51(d,2), 7.75(d,2), 7.83(m,2), 8.34(s,1).

Example 11

N-[1-[4-(1H-Imidazol-1-yl)-benzoyl]-4-piperidinyl]-2,6-dimethylbenzamide

In a manner similar to that described in Example 10, 1-[4-(1H-imidazol-1-yl)benzoyl]-4-piperidinamine dihydrochloride and 2,6-dimethylbenzoyl chloride are reacted to give the title compound.

We claim:
1. A compound of the following Formula I:

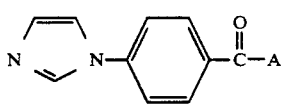

wherein
A is

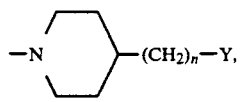

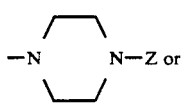

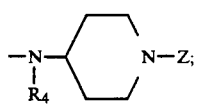

Y is

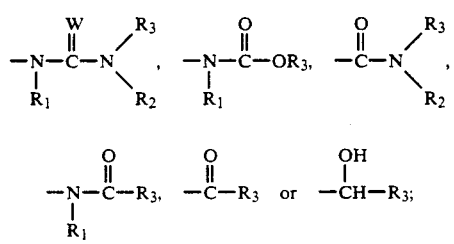

Z is

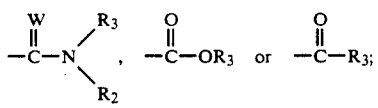

W is O, S, NR, NCN or CHNO$_2$;

R is selected from hydrogen, C$_1$-C$_4$ straight or branched chain alkyl, optionally substituted aryl or arylalkyl;

R$_1$, R$_2$, R$_4$ are independently hydrogen or C$_1$-C$_4$ straight or branched chain alkyl;

R$_3$ is selected from C$_1$-C$_8$ straight or branched alkyl, optionally substituted aryl or arylalkyl or heteroaryl;

n is the integers 0, 1 or 2, or a pharmaceutically acceptable salt thereof;

with the provisos that when R$_3$ is a C$_1$-C$_8$ straight or branched chain alkyl this is not inclusive of a tertiary moiety and when R$_3$ is heteroaryl, said heteroaryl cannot be attached to a hetero atom e.g. N or O.

2. A compound of claim 1 wherein A is

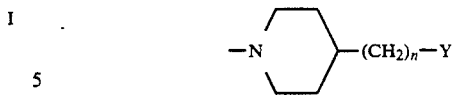

3. A compound of claim 1 wherein A is

4. A compound of claim 1 wherein A is

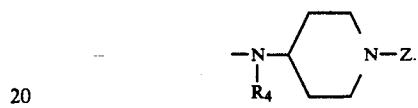

5. A compound of claim 2 which is N-butyl-N'-[1-[4-(1H-imidazol-1-yl)benzoyl]-4-piperidinyl]urea.

6. A compound of claim 2 which is N-butyl-N'-[1-[4-(1H-imidazol-1-yl)benzoyl]-4-piperidinyl]-N'-methylurea.

7. A compound of claim 2 which is N-butyl-N'-[1-[4-(1H-imidazol-1-yl)benzoyl]-4-piperidinyl]thiourea.

8. A compound of claim 2 which is 4-[[(3,5-dichlorophenyl)amino]carbonyl]amino-1-[4-(1H-imidazol-1-yl)benzoyl]piperdine.

9. A compound of claim 2 which is N-[[(3,5-dichlorophenyl)amino](imino)methyl]-1-[4-(1H-imidazol-1-yl)benzoyl]piperidine-4-amine.

10. A compound of claim 2 which is [1-[4-(1H-imidazol-1-yl)benzoyl]-4-piperidinyl]carbamic acid, butyl ester.

11. A compound of claim 2 which is N-butyl-1-[4-(1H-imidazol-1-yl)benzoyl]piperidine-4-carboxamide.

12. A compound of claim 2 which is N-[1-[4-(1H-imidazol-1-yl)benzoyl]-4-piperidinyl]hexanamide.

13. A compound of claim 2 which is N-[1-[4-(1H-imidazol-1-yl)benzoyl]-4-piperidinyl]benzenepropanamide.

14. A compound of claim 2 which is N-[1-[4-(1H-imidazol-1-yl)benzoyl]-4-piperidinyl]-2,6-dimethylbenzamide.

15. A compound of claim 2 which is N-[1-[4-(1H-imidazol-1-yl)benzoyl]-4-piperidinyl]-3-pyridinecarboxamide.

16. A compound of claim 2 which is 1-[4-(1H-imidazol-1-yl)benzoyl]-4-(1-oxohexyl)piperidine.

17. A compound of claim 2 which is 1-[4-(1H-imidazol-1-yl)benzoyl]-4-(1-oxoethyl)piperidine.

18. A compound of claim 2 which is 4-(1-hydroxyhexyl)-1-[4-(1H-imidazol-1-yl)benzoyl]piperidine.

19. A compound of claim 3 which is N-butyl-4-[4-(1H-imidazol-1-yl)benzoyl]piperazine-1-carboxamide.

20. A compound of claim 4 which is N-butyl-4-[[4-(1H-imidazol-1-yl)benzoyl]amino]piperidine-1-carboxamide.

21. The method of treating arrhythmias in a mammalian subject in need thereof comprising, administering to said subject an antiarrhythmically effective dose of a compound according to claim 1.

22. A pharmaceutical composition comprising a therapeutically effective amount of at least one compound according to claim 1, together with one or more nontoxic pharmaceutically acceptable carriers.

* * * * *

UNITED STATES PATENT AND TRADEMARK OFFICE
CERTIFICATE OF CORRECTION

PATENT NO. : 5,189,036
DATED : February 23, 1993
INVENTOR(S) : Chou, et al

It is certified that error appears in the above-indentified patent and that said Letters Patent is hereby corrected as shown below:

Column 6 - Scheme C

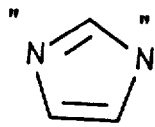 should read --- 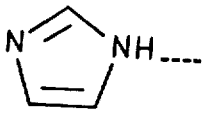 ----

Column 14, line 67

"Methylithium" should read --Methyllithium --.

Column 18, line 38

"2.96 (m,1), 3.73 (m,1), 4.63 (m,1)" should read ---- 2.96 (m,1), 3.13 (m,1), 3.73 (m,1), 4.03 (m,1), 4.63 (m,1), ----

Column 18, line 39

"7.45 (d,2), 7.90 (s,1)." should read ---- 7.45 (d,2), 7.54 (d,2), 7.90 (s,1). ----

UNITED STATES PATENT AND TRADEMARK OFFICE
CERTIFICATE OF CORRECTION

PATENT NO. : 5,189,036
DATED : February 23, 1993
INVENTOR(S) : Chou, et al

It is certified that error appears in the above-indentified patent and that said Letters Patent is hereby corrected as shown below:

Column 19, line 11

"piperidinyl]N'-methylurea" should read
---- piperidinyl]-N'-methylurea ----

Column 19, line 28

"3.01 (m,2), (br, m,1), 3.01 (m,2), 3.13 (br, m,1)"
should read ---- 3.01 (m,2), 3.13 (br m,1) ----

Signed and Sealed this

Twenty-fourth Day of May, 1994

Attest:

BRUCE LEHMAN

*Attesting Officer*   *Commissioner of Patents and Trademarks*